United States Patent
Rodriguez Y Baena

(10) Patent No.: US 8,303,575 B2
(45) Date of Patent: Nov. 6, 2012

(54) TOOL CONSTRAINT MECHANISM

(75) Inventor: Ferdinando Maria Rodriguez Y Baena, London (GB)

(73) Assignee: Stanmore Implants Worldwide Limited (GB)

( * ) Notice: Subject to any disclaimer, the term of this patent is extended or adjusted under 35 U.S.C. 154(b) by 1152 days.

(21) Appl. No.: 12/090,578

(22) PCT Filed: Aug. 18, 2006

(86) PCT No.: PCT/GB2006/003107
§ 371 (c)(1),
(2), (4) Date: Jul. 9, 2008

(87) PCT Pub. No.: WO2007/045810
PCT Pub. Date: Apr. 26, 2007

(65) Prior Publication Data
US 2009/0041565 A1 Feb. 12, 2009

(30) Foreign Application Priority Data
Oct. 19, 2005 (GB) .................................. 0521281.6

(51) Int. Cl.
*A61B 19/00* (2006.01)
(52) U.S. Cl. ........................................... 606/1; 606/130

(58) Field of Classification Search ............... 606/1, 130, 606/205
See application file for complete search history.

(56) References Cited

U.S. PATENT DOCUMENTS

| | | | |
|---|---|---|---|
| 4,669,483 A | 6/1987 | Hepp et al. | |
| 6,493,608 B1 | 12/2002 | Niemeyer | |
| 6,547,782 B1 | 4/2003 | Taylor | |
| 7,021,173 B2 | 4/2006 | Stoianovici et al. | |
| 2002/0120254 A1* | 8/2002 | Julian et al. | 606/1 |
| 2005/0043718 A1* | 2/2005 | Madhani et al. | 606/1 |
| 2006/0074406 A1* | 4/2006 | Cooper et al. | 606/1 |

FOREIGN PATENT DOCUMENTS

| | | |
|---|---|---|
| EP | 1 681 029 A1 | 7/2006 |
| JP | 2005-516786 | 6/2005 |
| WO | 03067341 A2 | 8/2003 |

* cited by examiner

*Primary Examiner* — Henry M Johnson, III
(74) *Attorney, Agent, or Firm* — Brooks Kushman P.C.

(57) ABSTRACT

A mechanism which constrains the spatial location of a working or a focal point of a tool (103), has a manipulator (101) and a remote center mechanism (102) mounted thereon. The manipulator (101) provides at least one degree of freedom for positioning the remote center mechanism (102) which itself provides at least a further degree of freedom for positioning a tool holder suitable for holding the tool (103) which is to be constrained in operation with respect to a remote center point. The orientation of the tool holder is adjustable while still maintaining the position of the remote center point fixed with respect to the manipulator (101).

12 Claims, 4 Drawing Sheets

TOOL CONSTRAINT MECHANISM

The present invention relates to a mechanism which constrains the spatial location of a working or a focal point of a tool; and in particular, although not exclusively, provides a constraint mechanism for use in medical robotic systems such as multi purpose bone sculpting carried out using a spherical cutter. Typical applications may include minimally invasive surgery, such as unicompartmental knee arthroplasty, pedicle screw insertion and hip arthroplasty.

Previous devices are known in the art for manipulation of surgical tools and restraint mechanisms. Such devices often involve large and complex motorised arms with 6 degrees of freedom positional tracking sensors. Such devices are both unwieldy, which impedes the subtle and intricate movements of tools often required during delicate surgery, and costly. For many applications, e.g. bone sculpting using a spherical cutter, control of only three degrees of freedom is sufficient to completely guide a sculpting tool. The position of the functioning end part of the tool, e.g. the actual spherical cutting bit, is required to be monitored, tracked and constrained, but the rotational orientation, e.g. pitch and yaw, of the functioning end of the tool and the tool itself is not important.

The present invention provides a tool constraint mechanism comprising a manipulator and a remote centre mechanism mounted thereon, the manipulator providing at least one degree of freedom for positioning the remote centre mechanism, and the remote centre mechanism providing at least a further degree of freedom for positioning a tool holder, said holder being suitable for holding a tool which is to be constrained in operation with respect to a remote centre point, the orientation of the tool holder being adjustable while maintaining the position of the remote centre point fixed with respect to the manipulator. Preferably, the manipulator may provide at least three degrees of freedom and the remote centre mechanism a further two.

Embodiments according to the present invention enable the spatial constraint of a working point of a tool, for example a spherical cutter, to within a safe region or working envelope while optimal tool orientation is left for the user, e.g. a surgeon, to control. This enables the tool to be freely rotationally orientated to avoid an obstruction and for ease of manipulation, whilst the functioning end of the tool is maintained in a safe working region, area or envelope. Embodiments according to the present invention can be used in any application requiring the working point of a tool to be constrained to a region but where the orientation of the tool is not necessarily required to be constrained. In some embodiments, the working point may be located at a functioning end of a tool (e.g. a cutter), while in others the working or target point may be located at a distance from the tool (e.g. a laser or an X-ray gun).

Preferably the manipulator 101 is back drivable, counterbalanced and motorised so that the links motion can be actively constrained to a predefined region inside which the user is free to drag the instrument around with minimal friction and effort. The links are also position encoded and can have brakes. Preferably, the manipulator comprises three degrees of freedom with three revolute joints, and the remote centre mechanism comprises two degrees of freedom with two revolute joints having a 360° range of motion.

The system may consist of a three-degrees-of-freedom serial Revolute-Revolute-Revolute (RRR) manipulator, with a waist joint, a shoulder joint and an elbow joint, and two additional non tracked/controlled joints in a remote centre motion configuration with the spherical cutter placed at the focal point. This allows the user to orient the tool for optimal entry without affecting the spherical cutter position, which is constrained by the first three (motorised) joints of the system.

The preferred embodiment could also include:
Encoders mounted on remote centre mechanism links to guide the user while orienting the tool.
Motors mounted on remote centre mechanism links to constrain orientation of the tool for full 3D robotic assistance.
A modular interlock to fit different remote centre mechanisms with different working envelopes for different applications.
A modular interlock to reorient the remote centre mechanism to suit different applications.

Possible other applications include sculpture work and training of complex hand motions. The invention extends to a method of surgery, of sculpture, and of training in the manual use of a tool.

Further advantages of embodiments according to the present invention are discussed below.

The present invention may be carried into practice in a number of ways, and several specific embodiments will now be described, by way of non limiting example, with reference to the accompanying drawings, in which.

Figure 1:
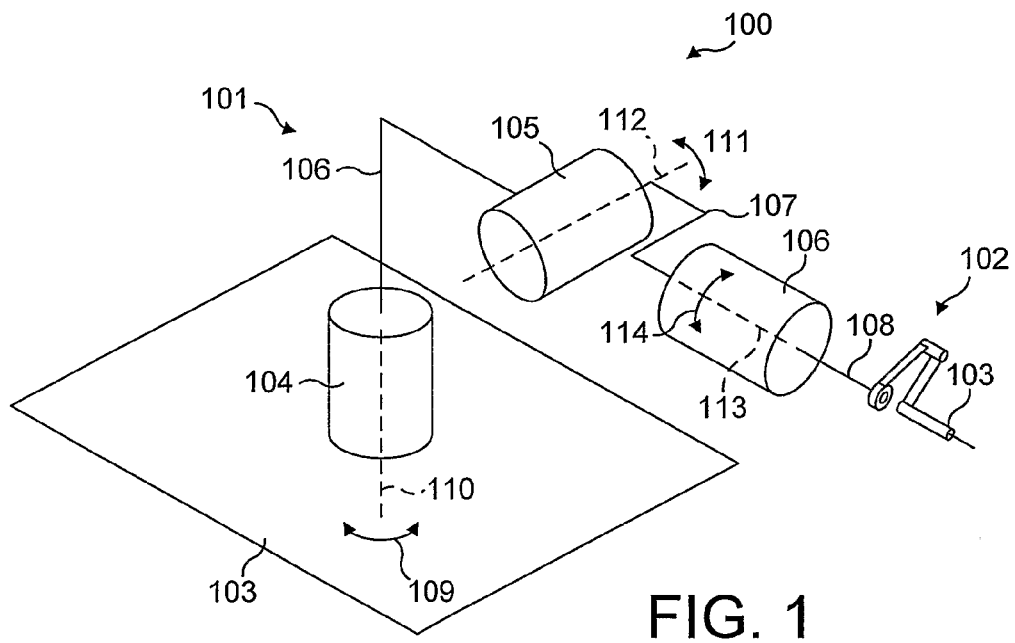
FIG. 1 is a schematic diagram of a first embodiment of a constraint mechanism according to the present invention.

As is schematically shown in FIG. 1, a constraint mechanism 100 according to a first embodiment of the present invention includes a manipulator 101, a remote centre mechanism 102 and a tool 103.

The manipulator 101 is attached to a base which provides a local frame of reference and secure grounding. The manipulator 101 includes revolute joints 104, 105 and 106 connected in series. Associated with each joint is a rigid link 106, 107 and 108 respectively, whose movements are constrained to those movements allowed by the joints. For each joint, 104, 105, 106 only rotation about the joint's central rotational axis 110, 112, 113 is permitted, as shown by the respective allows 109, 111, 114.

Figure 2:
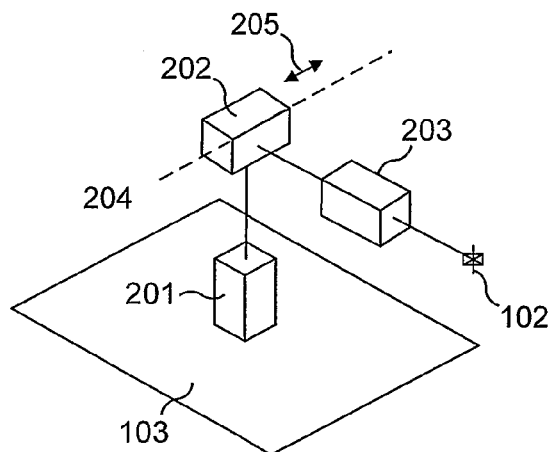
FIG. 2 is a schematic diagram of an alternative manipulator suitable for use with embodiments of a constraint mechanism according to the present invention.

An alternative embodiment, shown in FIG. 2, includes prismatic joints 201, 202, 203 rather than the revolute joints of FIG. 1. Each prismatic joint e.g. 202 allows only translational movement along the joint's axis 204, as shown by arrows 205.

Figure 3:
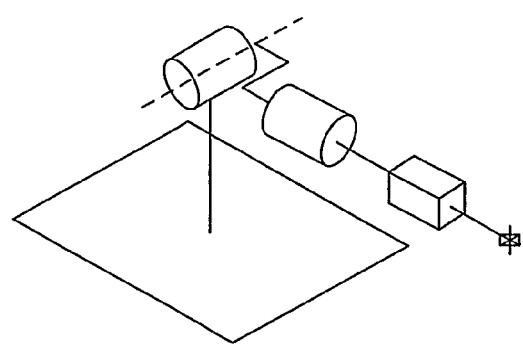
FIG. 3 is a schematic diagram of a further alternative manipulator suitable for use with embodiments of a constraint mechanism according to the present invention.

The joints can all be revolute joints as in FIG. 1, or all prismatic joints as in FIG. 2, or a mixture of revolute, prismatic or other types of joints such as a ball and socket joint, as shown in FIG. 3. Also, the rigid links need not be straight, but can be of any shape; for example link could contain a single bend such as the link 106 or multiple bends as in the link 107.

The links and joints are connected together in series which increase the number of degrees of freedom of a distal end of the manipulator, the final link 108, and enable more complex movement of the distal end. As shown in FIG. 1, the joint 104 is secured to the base. The joint 105 is attached to the link 106, which is associated with the joint 104. The link 107, which is associated with the joint 105, can not only rotate about the rotation axis 112 of the joint 105, as shown by the arrow 111, but it is additionally able to rotate about the axis 110 of the joint 104, as shown by the arrow 109. The joint 106 is attached to the link 107. The link 108, which is associated with the joint 106, can therefore rotate about the axes of rotation 113, 112 and 110. The remote centre mechanism 102 is attached to the distal end of the manipulator at link 108, which is itself coupled to the tool 103.

The manipulator can have one of many kinematic configurations, including but not restricted to those discussed above with reference to FIGS. 1, 2 and 3.

Figure 4A:
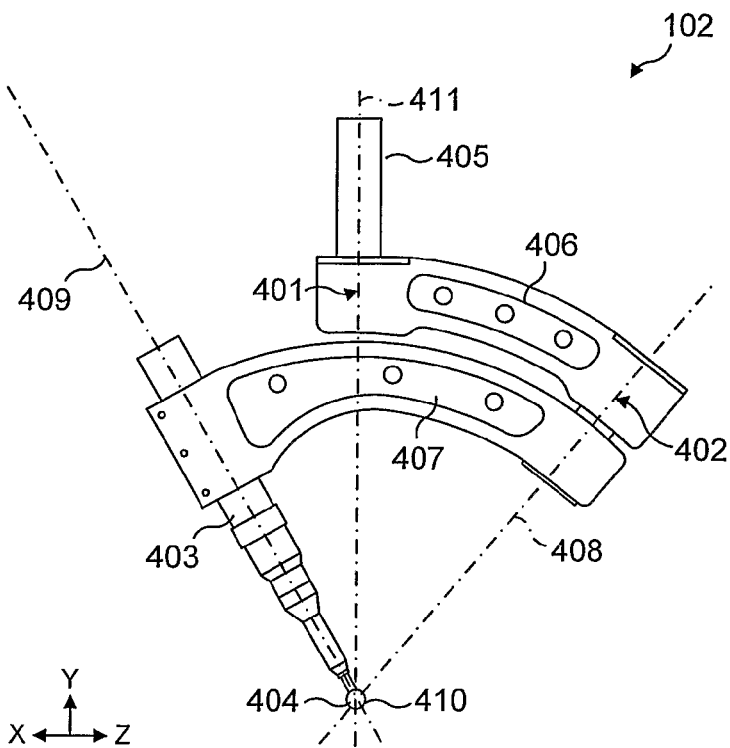
FIGS. 4A, 4B and 4C show perspective views of a remote centre mechanism suitable for use with embodiments of a constraint mechanism according to the present invention.
Figure 4B:
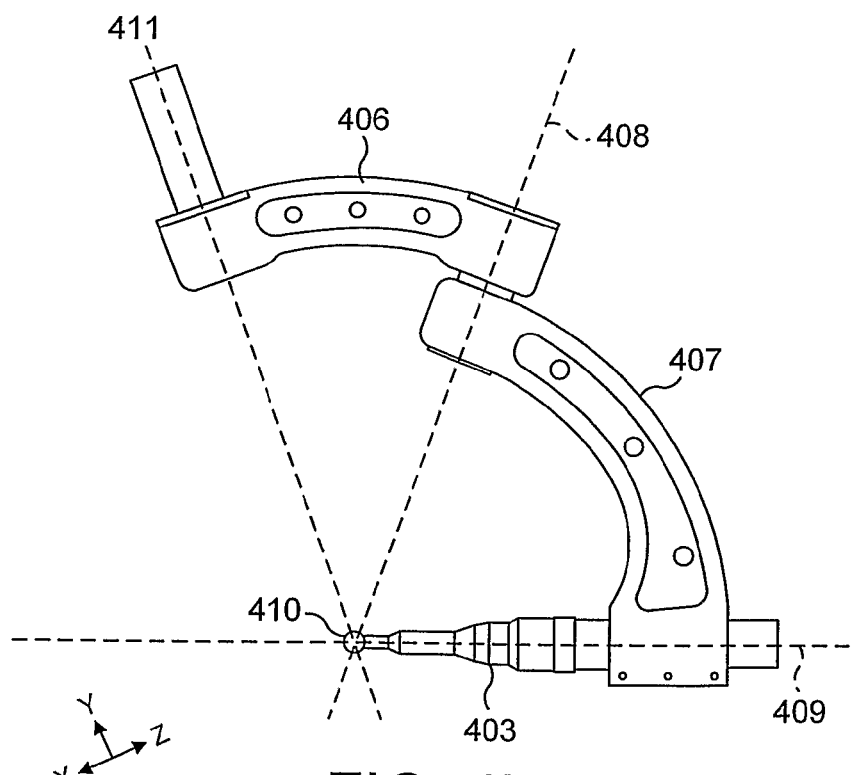
Figure 4C:
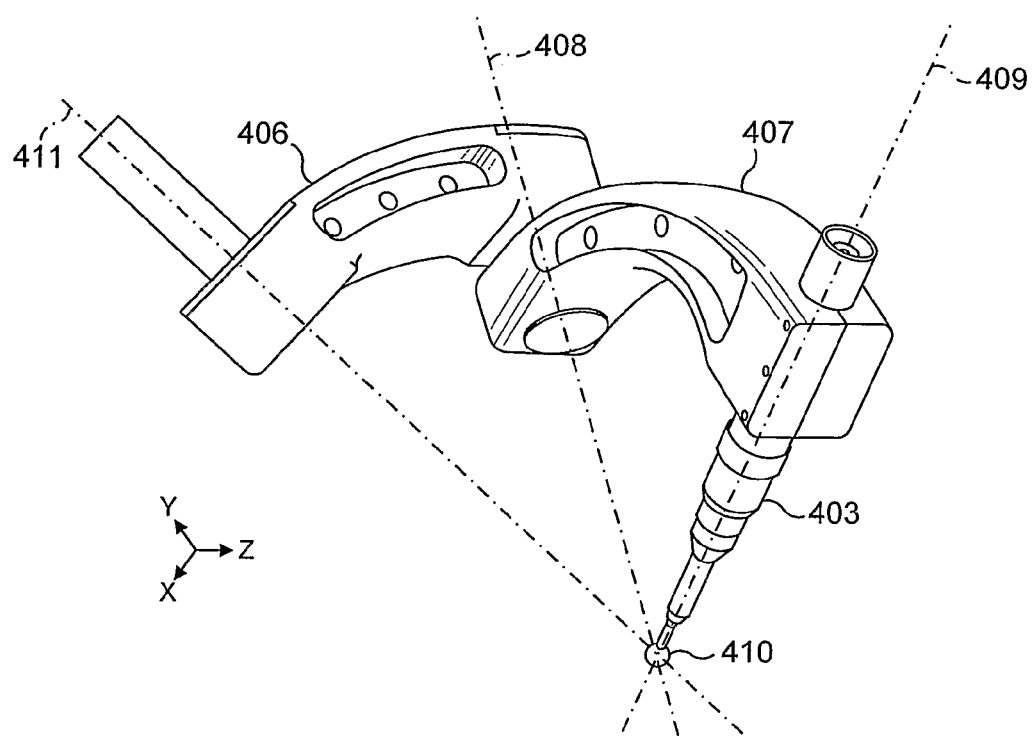

FIGS. 4A, 4B and 4C illustrate an embodiment of the remote centre mechanism 102 which is shown schematically in FIG. 1. The purpose of the remote centre mechanism is to hold a tool in a so called remote centre configuration, whereby several rotational degrees of freedom of the tool, such as its orientation, (eg Yaw, Pitch and Roll) can be varied by the user while maintaining a fixed remote centre or target point of the tool. In the embodiment of FIG. 4, the tool is a cutter 403 having a functioning end or cutting point 404. In this embodiment, the purpose of the remote centre mechanism is to hold the cutting point 404 stationary at a remote centre 410, regardless of the orientation of the tool 403 itself.

The remote centre mechanism 102, shown in FIG. 4, has a mounting rod 405 allowing it to be coupled to a distal end of a manipulator, for example of the form shown in FIG. 1. The remote centre mechanism is secured to the manipulator so that the distal axis 108 of FIG. 1 is co-incident with a first axis 411 of the remote centre mechanism.

Coupled to the mounting rod 405 by a joint 401 is a first link 406. The joint 401 allows this link to rotate freely around the first axis 411.

At the distal end of the link 406 is a second joint 402 defining a second axis 408. Coupled to this joint is a second link 407, this link being freely rotatable around the second axis 408.

At the distal end of the second link 407 is mounted the cutting tool 403. The cutting tool is generally pen shaped, for easy graspability and manual manipulation by the surgeon, and lies along a tool axis 409.

The tool in this and other embodiments may also include an ergonomic sleeve (not shown) which is able to freely rotate about the tool axis. The sleeve, which does not move in any direction apart from rotating around the axis of the tool, enables the tool to be gripped without this action constraining the motions of the remote centre mechanism—i.e. the user will hold onto the tool via the ergonomic handle or sleeve, which will slide over the tool to produce smooth, substantially frictionless dragging of the constrained mechanism during use.

The orientations of the revolute joint 401, the revolute joint 402 and the tool 403 are arranged so that the three axes 411, 408 and 409 intersect one another at the same spatial location point, the remote centre 410.

With this arrangement, the remote centre 410 remains fixed in location when the link 406 rotates around the axis of rotation 411, and when the link 407 rotates around the axis of rotation 408.

The rotational degree of freedom provided by the joint 401 enables the yaw movement of the tool to be freely altered by the surgeon whilst keeping the remote centre 410 constant, as may be seen in FIG. 4B. Pitch movement of the tool can be freely altered via a combination of rotation of both joints 401 and 402, as may be seen in FIG. 4C.

The addition of a further revolute joint (not shown) located such that its axis of revolution is co-axial with the tool axis 409, and would therefore also intersect the other axes at the remote centre 410, could provide roll rotational movement of the tool. Of course for some applications, such as where the tool is a spherical cutter, roll rotation of the tool is not necessary.

The spatial location of the remote centre 410 is controlled and/or tracked by the manipulator 101. The joints of the manipulator can be motorised and/or monitored or position-encoded so that the location of the remote centre can be precisely controlled, monitored and tracked. The links of the manipulator 101, whether motorised or not, may be manually adjusted by the user. In some embodiments, this may conveniently be achieved simply by allowing the user to pull/push the tool or the remote centre mechanism, with the joints of the manipulator being left free to move.

In one embodiment, the links 406, 407 may be removable, and may be replaced with links of differing lengths, shapes and configurations, to be chosen according to the application in hand. By selecting different link combinations the user may select a variety of different freedoms of movement for the tool.

Figure 5:
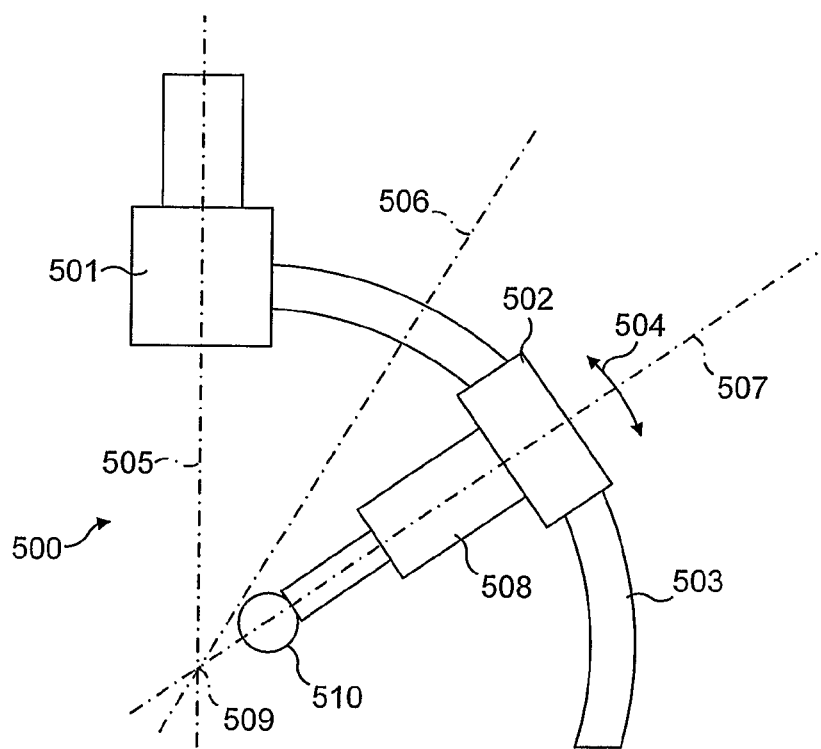
FIG. 5 shows an alternative remote centre mechanism suitable for use with embodiments of a constraint mechanism according to the present invention.

Another remote centre mechanism 500 is shown in FIG. 5. Two degrees of freedom of movement of the tool are provided by a revolute joint 501 and a prismatic joint 502 that traverses along an arc track 503 as shown by arrows 504. The axis of rotation of the revolute joint 501 defines a first axis 505. A line perpendicular to the tangent of the arc track defines a second axis 506. The longitudinal axis of the tool 508 defines a tool axis 507.

The shape of the arc track 503, and the orientations of the revolute joint 501 and the tool 508 are such that the three axes 505, 506 and 507 intersect at a single remote centre 509. The revolute joint 501 controls the yaw of the tool and the prismatic joint 502 traversing along the arc track 503 controls the pitch of the joint. Whilst the yaw and pitch of the tool 508 change the spatial location of the remote centre 509 remains constant.

In this embodiment, the tool holder could slide along the arc track 503, or alternatively the track itself could slide with respect to the joint 501, with the holder being fixed in place on the track.

Alternative configurations are possible to achieve remote centre motion for the remote centre mechanism, for example cam mechanisms and four-bar linkages. The choice of configuration depends on the range of motion requirements of the system, which in turn depend on the application.

In FIG. 4, the tool is aligned and positioned such that its functioning end 404 is located at the remote centre 410. In such a configuration, when the pitch and yaw of the tool is altered, e.g. by a surgeon operating the tool during surgery, the functional end of the tool is kept in the same spatial location.

In FIG. 5, in contrast, a functional end 510 of a tool 508 is located just short of the remote centre 509. In such a configuration, when the yaw and pitch of the tool is altered, the spatial location of the functional end does not remain constant but follows either a circular path, an arc path or a concave surface depending on whether just the yaw (revolute joint rotates), pitch (just the prismatic joint traverses along the arc track) or both yaw and pitch are altered (both joints move) respectively. If the functional end of the tool were to be located to the other side of (beyond) the remote centre, the spatial location of the end would follow either a circular path, an arc path or convex surface depending on whether just the yaw, pitch or both yaw and pitch are altered respectively. Of course, the functional end of the tool could, in appropriate circumstances, be positioned exactly on the remote centre 509, as with the FIG. 4 embodiment.

The allowable range of movement of the functional end of the tool (with respect to a fixed manipulator) is defined by the remote centre mechanism and the location of the functional end of the tool with respect to the remote centre. This is the region or envelope in which the functional end of the tool can be freely moved by the user. The working envelope can comprise a single point (the remote centre), circular paths, arc paths, and concave or convex surfaces. Additionally, the working surfaces can be further refined by placing limits on the allowed movement on the joints by restricting their range of motion, e.g. restricting the rotation of the revolute joints to certain angles, restricting the translation of prismatic joints to pre-set lengths, and so on. This could be done in any convenient way, for example by the use of stops (not shown).

Unhindered and free movement of the pitch and yaw orientation of a cutting tool, such as a spherical cutter, is often convenient to aid the surgeon during the machining process, but such movement does not necessarily need to be controlled or tracked. Often, only the position of a functional end of the tool needs to be controlled and/or tracked. Sometimes the entire tool location and orientation may not matter at all, provided that the tool target or working point remains stationary (e.g. High Intensity Focused Ultrasound (HIFU) treatment, where it is intended to make various transducers focus on the same point).

The position of the remote centre 410 can be moved, controlled and tracked by the motorised manipulator 101 whilst the pitch and yaw orientation of the tool can be altered and freely controlled by the tool operator. Thus, the described embodiments allow the operator to orient the tool for optimal access without affecting the spherical cutter position (this being constrained by the joints of the manipulator) at a very low cost since the remote centre mechanism neither requires motorised joints nor tracking of its links. Of course, tracking and/or motorisation of the remote centre mechanism links is not excluded.

Figure 6:
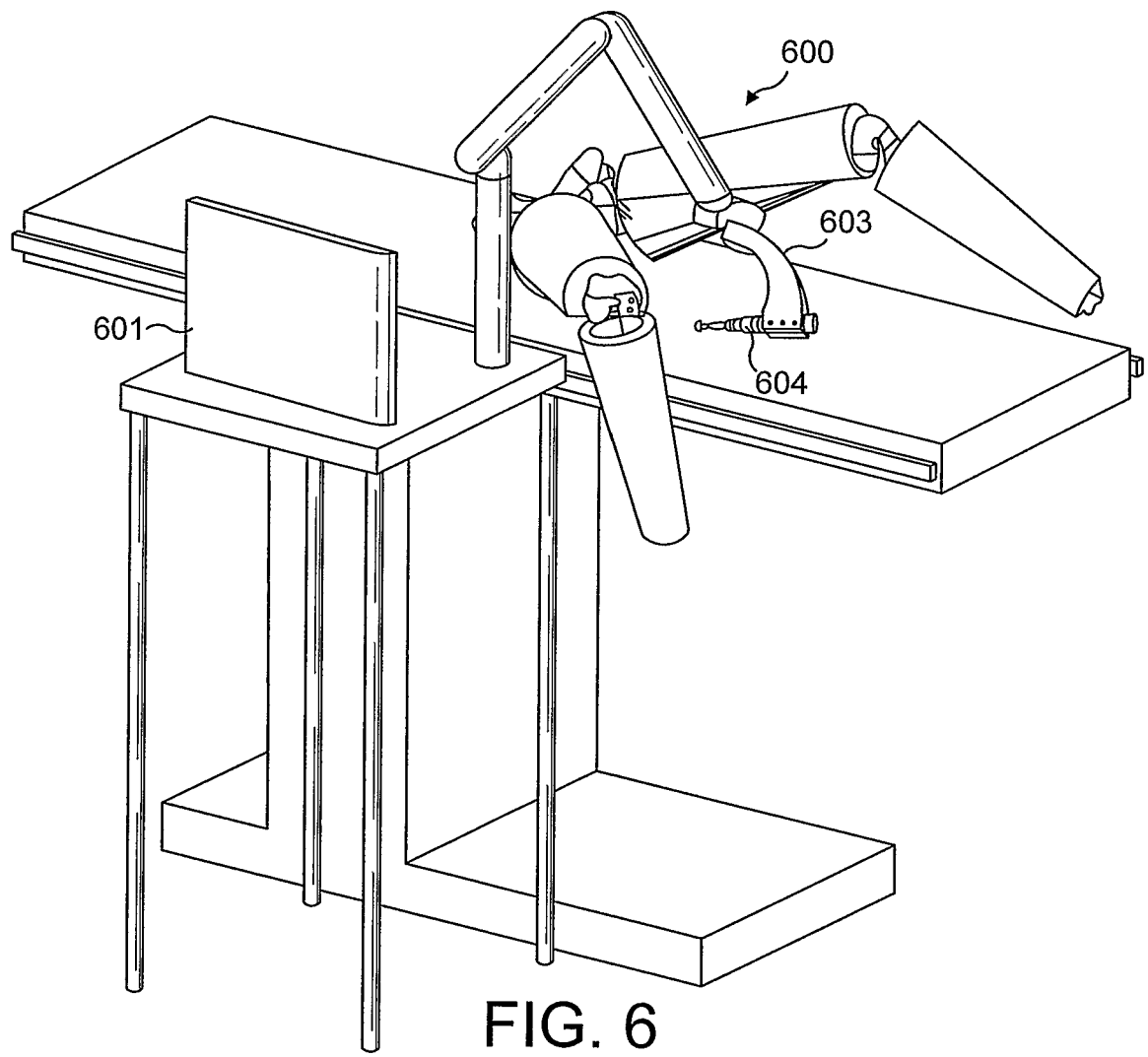
FIG. 6 shows an embodiment of a constraint mechanism according to the present invention.

FIG. 6 shows a constraint mechanism according to a further embodiment of the present invention. A control panel 601 controls the motorised joints of a manipulator 600 whilst a remote centre mechanism 603 is non-motorised and allows free rotational movement of a tool 604 about a remote centre. Alternatively, the panel may simply be a display giving visual guidance to the surgeon, with motion being controlled by the surgeon's direct handling of the manipulator, or via a pre-programmed set of manipulator motions. In such an arrangement, the panel may provide the means to program the system.

When embodiments according to the present invention are used to drill deep holes for example with a spherical cutting tool, the working tool end is constrained by the manipulator, while the user ensures the shaft of the cutter does not collide with the sides of the hole being machined. The operator can achieve complete synergy between the machine-controlled manipulator and the freely-moveable remote centre mechanism.

The position of the functional end of the tool can be achieved through accurate manufacture of a tool attachment element which is connected to the remote centre mechanism, or by the addition of a tuning mechanism to the end of the remote centre mechanism's distal link. The tuning mechanism could take a number of shapes, but should enable the position of the functional end of the tool, e.g. centre of a cutting bit, to be adjusted so that it is located at the intersection between the two joints axes. The two joints axes can be manufactured so that they are coplanar.

Embodiments according to the present invention are particularly suited to minimally invasive surgery, since all five degrees of freedom can be designed to be at a distance from the remote centre, which might need to be embedded deep into the tissue through a small incision.

Additional embodiments (not shown) could also include encoders mounted on the remote centre mechanism links, to guide the user while orienting the cutter. Motors could also be mounted on the remote centre mechanism links to constrain orientation of the cutter for full robotic assistance in 5, 6 or more degrees of freedom.

The constraining mechanism may comprise a modular and replaceable (interlock) system for connecting the remote centre mechanism to the manipulator, thus allowing remote centre mechanisms with different working envelopes to be easily fitted onto the manipulator for different applications. The modular interlock could also be arranged to be able to reorient the remote centre mechanism to suit different applications.

Several constraint mechanisms can be combined to work in collaboration. It is also possible to have more than one remote centre mechanism mounted on the same manipulator. This would enable, for instance, High Intensity Focused Ultrasound (HIFU) treatment, where it is intended to make various transducers focus on the same point.

It will be appreciated that the device as described above could equally well be any other implement or apparatus, with a functional end, e.g. a measuring probe tip, X-ray, ultrasound or laser emitter, whose target or focus location needs to be precisely motion controlled and tracked, but where rotational and/or spatial location of the functional end need not be precisely known and tracked. Thus the tool can be freely orientated as required by the user whilst the target location is tracked and/or kept in the required position.

What is claimed is:

1. A tool constraint mechanism comprising a manipulator and a remote center mechanism mounted thereon, the manipulator providing at least one degree of freedom for positioning the remote center mechanism, and the remote center mechanism providing further degrees of freedom for positioning a tool holder, said holder being suitable for holding a tool which is to be constrained in operation with respect to a remote center point, the orientation of the tool holder being adjustable while maintaining the position of the remote center point fixed with respect to the manipulator; wherein the remote center mechanism comprises a first rigid link coupled to the manipulator by a first revolute joint for rotation about a first axis, and a second rigid link coupled to the first rigid link by a second revolute joint for rotation about a second axis, the tool holder being mounted onto or forming part of the second link, with the first and the second axes intersecting at the remote center, the mechanism being characterised in that the first revolute joint is at a first end of the first rigid link, and that the tool holder is at a distal end of the second rigid link.

2. A tool constraint mechanism as claimed in claim 1 in which at least one remote center mechanism joint is motorized.

3. A tool constraint mechanism as claimed in claim 1 in which at least one remote center mechanism joint is position-tracked.

4. A tool constraint mechanism as claimed in claim 1 in which the tool holder provides a rotational mounting for a tool when held by the tool holder.

5. A tool constraint mechanism as claimed in claim 1 including a tool held by the tool holder.

6. A tool constraint mechanism as claimed in claim 5 in which the tool has a functional end which is held by the remote center mechanism at the remote center.

7. A tool constraint mechanism as claimed in claim 5 in which the tool has a functional end which is held by the remote center mechanism spaced from the remote center, the functional end thereby being held on a defined surface as the tool is positioned by the remote center mechanism.

8. A tool constraint mechanism as claimed in claim 5 in which the tool is manually graspable, its orientation being manually adjustable by a user.

9. A tool constraint mechanism as claimed in claim 5 in which the tool is a cutter.

10. A tool constraint mechanism as claimed in claim 5 in which the tool is a laser or an irradiation device.

11. A tool constraint mechanism as claimed in claim 5 in which the tool is a surgical instrument.

12. A tool constraint mechanism as claimed in claim 5 in which the tool is surrounded by a manually-graspable rotatable sleeve.

* * * * *